United States Patent [19]
Olstad et al.

[11] Patent Number: 5,820,561
[45] Date of Patent: Oct. 13, 1998

[54] ANALYSIS AND MEASUREMENT OF TEMPORAL TISSUE VELOCITY INFORMATION

[75] Inventors: Bjørn Olstad, Langesund, Norway; Lars Åke Brodin, Taby, Sweden; Kjell Kristoffersen, Oslo, Norway

[73] Assignee: Vingmed Sound A/S, Horten, Norway

[21] Appl. No.: 719,364

[22] Filed: Sep. 25, 1996

[30] Foreign Application Priority Data

Jul. 30, 1996 [NO] Norway .................................. 963175

[51] Int. Cl.$^6$ ...................................................... A61B 8/00
[52] U.S. Cl. ............................................ 600/453; 600/449
[58] Field of Search ........................ 128/660.04, 660.07, 128/661.04, 661.09, 661.1, 916; 600/440, 449, 453, 443, 454–456

[56] References Cited

U.S. PATENT DOCUMENTS

| | | | |
|---|---|---|---|
| 4,398,540 | 8/1983 | Takemura et al. | 128/660 |
| 4,501,277 | 2/1985 | Hongo | 128/660 |
| 4,509,525 | 4/1985 | Seo | 128/663 |
| 5,165,413 | 11/1992 | Maslak et al. | 128/660.05 |
| 5,170,792 | 12/1992 | Sturgill et al. | 128/661.09 |
| 5,197,477 | 3/1993 | Peterson et al. | 128/661.08 |
| 5,285,788 | 2/1994 | Arenson et al. | 128/660.05 |
| 5,329,929 | 7/1994 | Sato et al. | 128/660.65 |
| 5,353,220 | 10/1994 | Ito et al. | 364/413.13 |
| 5,355,887 | 10/1994 | Iizuka et al. | 128/660.04 |
| 5,379,769 | 1/1995 | Ito et al. | 128/660.07 |
| 5,412,764 | 5/1995 | Tanaka | 395/124 |
| 5,413,105 | 5/1995 | Forestieri | 128/660.05 |
| 5,415,171 | 5/1995 | Goh et al. | 128/660.07 |
| 5,425,365 | 6/1995 | Iinuma | 128/660.05 |
| 5,513,640 | 5/1996 | Yamazaki et al. | 128/661.09 |
| 5,515,856 | 5/1996 | Olstad et al. | 600/440 |
| 5,568,812 | 10/1996 | Murashita et al. | 600/440 |
| 5,615,680 | 4/1997 | Sano | 128/661.09 |
| 5,622,174 | 4/1997 | Yamazaki | 128/661.09 |

FOREIGN PATENT DOCUMENTS

| | | |
|---|---|---|
| 6285064 | 10/1994 | Japan . |
| 6292666 | 10/1994 | Japan . |
| 6315483 | 11/1994 | Japan . |

*Primary Examiner*—Francis Jaworski
*Attorney, Agent, or Firm*—Rothwell, Figg, Ernst & Kurz

[57] ABSTRACT

A method for extracting anatomical M-Mode displays of tissue velocity information along arbitrary curved polygons that can track curved organs such as myocard is described. The generated images can display the temporal velocity variations in a curved organ such as myocard in a single view. Time delays between events can be measured from these images. Furthermore, the invention describes how the time delay of characteristic events in temporal velocity evolutions and information derived from these velocity evolutions can be integrated into spatial time delay images that show the spatial propagation of the selected phenomenon. The characteristic events include switch in velocity direction, peak velocity, peak acceleration and similar aspects of tissue thickening. These characteristic events will be almost angle independent even if the tissue velocity is estimated with a Doppler technique along the propagation direction of the ultrasound beam. The invention further describes how the information extracted in a curved anatomical M-Mode can be utilized to estimate the phase of the regional wall motion in cardiac studies. It is also described how the phase of the regional wall motion can be estimated for all points in the imaged spatial region and displayed as a spatial map of the regional wall motion phase.

38 Claims, 4 Drawing Sheets

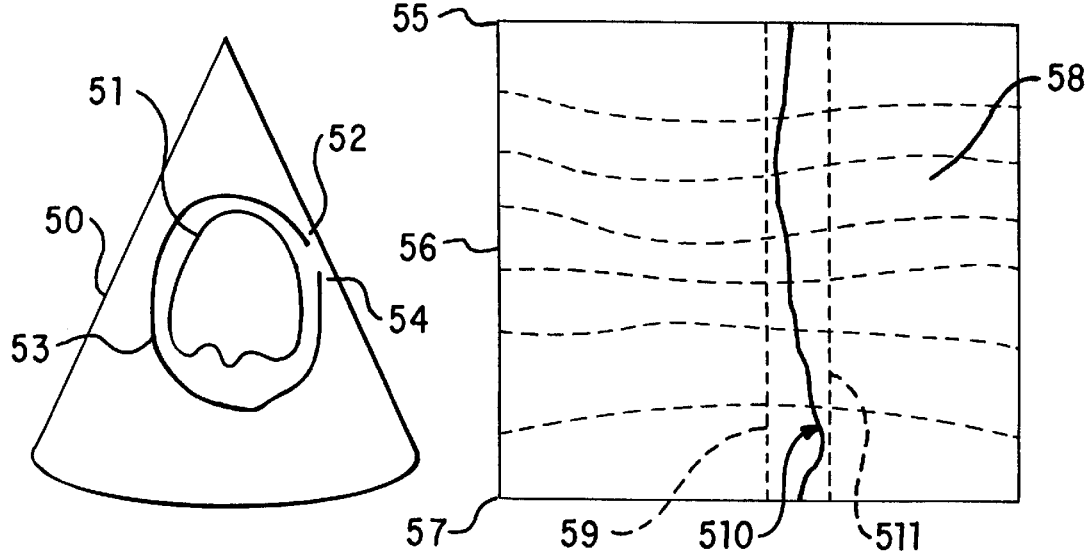
FIG. 5A
FIG. 5B
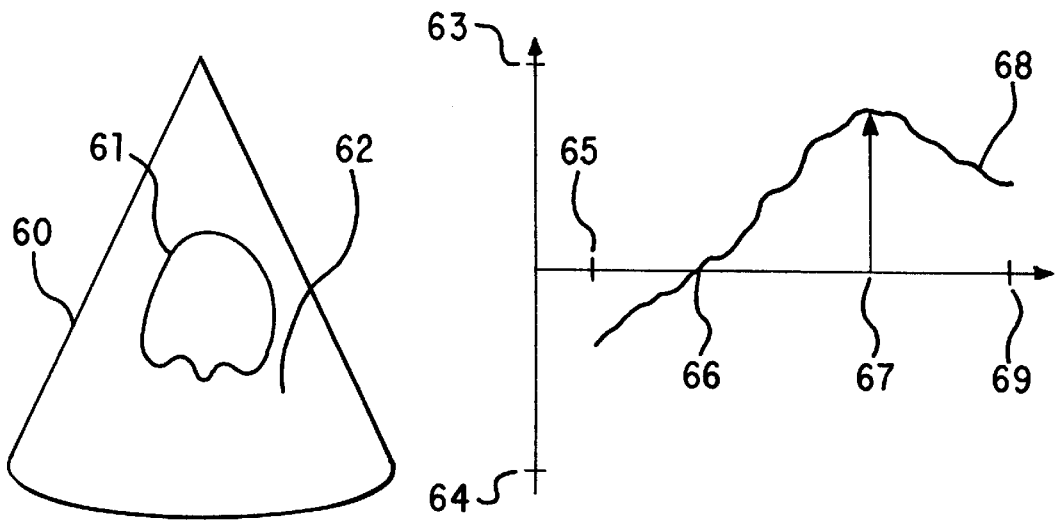
FIG. 6A
FIG. 6B

ANALYSIS AND MEASUREMENT OF TEMPORAL TISSUE VELOCITY INFORMATION

BACKGROUND OF THE INVENTION

1. Field Of The Invention

The invention relates generally to the field of ultrasound diagnosis of living biological structures, and more particularly to methods for analyzing, measuring and displaying the temporal variations of the velocities measured in biological structures.

2. Description Of The Background Art

Techniques for real-time acquisition of a sequence of ultrasonic images with coregistered tissue and tissue velocity information are well known. The velocity information can currently be obtained with:

1. a 1-dimensional velocity estimation with Doppler techniques along the propagation direction of the ultrasound beam, or
2. a 2-dimensional velocity estimation with Doppler techniques along the propagation direction of two skewed ultrasound beams, or
3. a spatial displacement correlation between subsequent ultrasound images.

The above techniques can be applied to a predetermined region in a 2-dimensional ultrasound image to create an image displaying aspects of the tissue velocities at a given time instant. Modern digital ultrasound scanners can generate such images with frame rates up to and exceeding 100 frames per second. The anatomical M-Mode technique described in the U.S. Pat. No. 5,515,856, entitled "Method For Generating Anatomical M-Mode Displays," can be used to extract the measurements along an arbitrarily positioned line across the 2D image and display this information versus time as in a conventional M-Mode image. The timing information is utilized to characterize the functionality and movement of the studied biological structure.

SUMMARY OF THE INVENTION

The invention described and claimed herein relates to a temporal analysis of the velocity evolution at every point in the spatial region where tissue velocity measurements are performed. Characteristic features with the associated timing indicators are extracted for every point in the said spatial region and displayed coregistered with the underlying tissue images. The resulting images can in a single view show the spatial propagation of the phenomenon associated with the selected characteristic feature, such characteristic features including switch in velocity direction, peak velocity, peak acceleration and tissue thickening.

Furthermore, the invention describes how velocity information can be extracted along an arbitrary geometrical shape and displayed versus time as in a conventional M-Mode image. The arbitrary shape allows the operator to create images that display the velocity variations in a curved organ such as myocard versus time in a single image. The invention also describes how these two techniques can be combined to create a tool that allows for precise spatial and temporal localization of motion phenomena such as motion disorders.

The techniques of the invention have a number of clinical applications related to timing information of the movement of biological structures. One such example is the study of wall movement in echo cardiography. The invention provides techniques for describing precisely the temporal and spatial localization of phenomena such as acceleration and retardation. With sufficient temporal resolution this makes noninvasive electrophysiology possible. The invention makes it possible to accurately determine the localization of where the mechanical movement in the heart chambers is activated based on a cross section just below the AV-plane. Furthermore, aberrant conduction pathways (Wolf-Parkinson-White) from the atrium to the ventricle can be localized for later ablation. Even the depth inside myocard of these paths can be better localized with this invention in order to determine if the patient should be treated with catheter techniques or surgical techniques.

The invention provides techniques that can be used to give an accurate description of both the spatial and temporal extent of distortions in the movement. The possibility of plotting variations of velocities inside myocard is also important in the diagnosis of rejection after heart transplantation.

The extraction of characteristic velocity features with associated time indications for a spatial region differs from background art in that, among other things, a single image can display the temporal propagation of the selected phenomenon within the imaged spatial region.

The invention includes preprocessing algorithms of the velocity information which differs from background art in that, among other things, it produces reliable temporal localization of derived characteristic points and thus allows for a smooth mapping of the selected features over the imaged spatial region.

The invention localizes characteristic features such as switch in velocity direction, peak velocity, peak acceleration and tissue thickening with subpixel techniques which differ from the background art in that, among other things, the measurements and display of temporal localization can be improved with typically a factor of 3–10 compared to the framerate. Hence, the technique can be used with current ultrasound technology to map velocity dynamics with a temporal resolution of 2 ms over a full 2D sector.

The arbitrary geometrical shape utilized in the anatomical M-Modes differs from background art in that, among other things, curved organs such as myocard can be tracked allowing for visual inspection and documentation of the velocity evolutions in a single M-Mode image. Several heartbeats can be tracked in this manner and the resulting anatomical M-Modes can in this case monitor the effects of an injection of an ultrasonic contrast agent. This technique can be used to obtain qualitative and quantitative perfusion information from the studied organ including perfusion studies in myocard.

The invention describes methods for using anatomical M-Modes described in the U.S. Pat. No. 5,515,856, the entire disclosure of which is incorporated herein by reference, and the curved anatomical M-Mode described in this invention as both a tool for identifying motion phenomena and as a tool for specifying the temporal region of interest that should be utilized in the analysis and display of the spatial propagation described in this invention. The combination of the anatomical M-Mode, the curved anatomical M-Mode and the mapping of velocity phenomena across a spatial region differs from background art in that, among other things, it provides an environment where the operator can select arbitrary space versus time displays of the velocity information to identify clinically important phenomena. Furthermore, the spatial mapping of characteristic features and associated time localization can be directly related to space versus time plots of the velocity information.

The invention differs from background art in that, among other things, the timing information displayed over a spatial region is approximately direction insensitive even if only the 1-dimensional component along the ultrasonic beam of the 3-dimensional velocity vector has been estimated. The approximation is valid if the direction of the 3-dimensional velocity vector at a given spatial point remains fixed or has only minor low-frequency variations during the time interval that is analyzed. Many characteristic points of the velocity evolution such as the time of velocity reversal, peak velocity and peak acceleration will in this case be independent of the direction of the ultrasound beam.

The invention describes how multiple curved anatomical M-Modes can be generated to display the velocity variations from for example endocard to epicard. The usage of multiple curved and/or straight anatomical M-Modes extracted from the same ultrasonic acquisition sequence differs from background art in that, among other things, it becomes possible to measure and quantify delays between all parts of the imaged spatial region. The alternative usage of multiple acquisition sequences is inadequate because variations in heartrate often exceed the time intervals that carry important clinical information in the study of motion delays.

The invention also describes how the tissue velocity information can be used to automatically reposition an anatomical M-Mode or a curved anatomical M-Mode such that the line or curved geometry intercepts the tissue at the same physical location during motion of the imaged biological structure. One example of this technique is the possibility to fix an anatomical M-Mode line at a given point in myocard and let the line move with the velocity information measured at the fixation point in myocard.

The invention describes how the regional phase of the wall motion in cardiac studies can be computed based on the tissue velocity data. The method is based on analysis of the velocity information extracted in anatomical M-Mode displays and curved anatomical M-Mode displays of tissue velocity data.

As described in column 2 of U.S. Pat. No. 5,515,856, computer processings of data sets and the like techniques were previously known, such as seen, for example, in the references cited on column 2 of the '856 Patent. As in the '856 patent, such computer processings in the implementations of the present invention would be within the realm of one of ordinary skill in the art, and, thus, further discussions thereof are omitted herein-below. For reference, some other documents relating to background techniques are as follows:

1) Peter Seitz, "Optical Super resolution Using Solid State Cameras And Digital Signal Processing", *Optical Engineering* 27(7) Jul. 1988.
2) Jørgen Mæhle et al., "Three-Dimensional Echo cardiography For Quantitative Left Ventricular Wall Motion Analysis: A Method For Reconstruction Of Endocardial Surface And Evaluation Of Regional Disfunction", *Echocardiography* 1994-11,4 page 397–408.
3) Knut Bjørnstad et al., "Quantitative Computerized Analysis Of Left Ventricular Wall Motion", *In Computerized Echocardiography*. Pezzano 1993 page 41–55.

The above and other advantages, features and aspects of the present invention will be more readily perceived from the following description of the preferred embodiments thereof taken together with the accompanying drawings and claims.

BRIEF DESCRIPTION OF THE DRAWINGS

The present invention is illustrated by way of example and not limitation in the accompanying drawings, in which like references indicate like parts, and in which:

FIGS. 5(A) and 5(B) show a curved anatomical M-Mode and a characteristic features in the velocity evolution that has been indicated for each spatial coordinate. In addition, the figure illustrates how the user can indicate in this image a time period across the selected feature to be further analyzed in a spatial context.

FIGS. 6(A) and 6(B) illustrate the velocity evolution for a given spatial point during the selected time interval.

DETAILED DESCRIPTION OF THE PREFERRED EMBODIMENTS

Figure 1A:
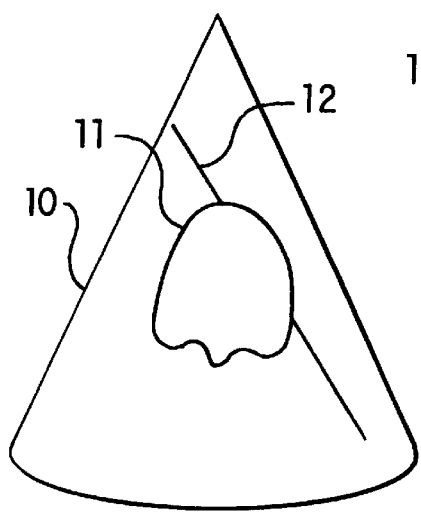
FIGS. 1(A) and 1(B) show an anatomical M-Mode which is associated with an arbitrarily positioned line across a 2D image.
Figure 1B:
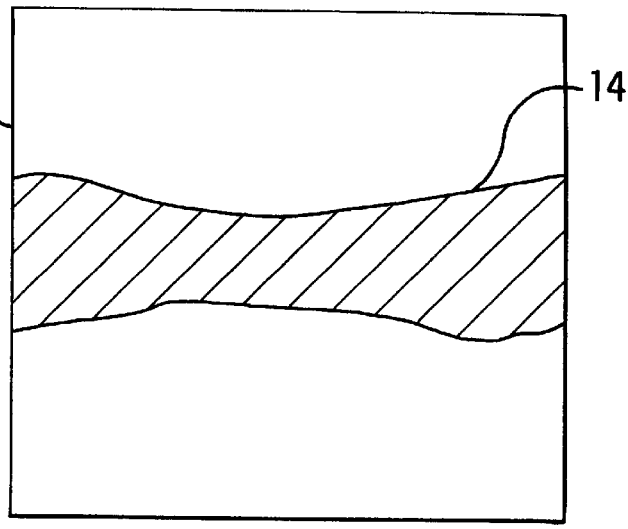

The acquisition of ultrasonic image frames and computation of tissue velocities are considered as background art. According to the present invention, the anatomical M-Mode displays taught in U.S. Pat. No. 5,515,856 (discussed above), the disclosure of which is incorporated herein by reference, can be applied to the extraction of tissue velocity information. Referring first to FIG. 1, an ultrasonic image with an associated anatomical M-Mode display is shown. The ultrasonic sector is given by 10. An arbitrary biological structure 11 is illustrated inside the imaged spatial region. A straight line identifying the position of an anatomical M-Mode is indicated 12 as taught in U.S. Pat. No. 5,515, 856. The associated anatomical M-Mode display is shown 13 with an indication of the time dependence 14 of the interception with the selected example of a biological structure. Applied to tissue velocity information 13 will render the time variation of the tissue velocity across the line 12.

Figure 2A:
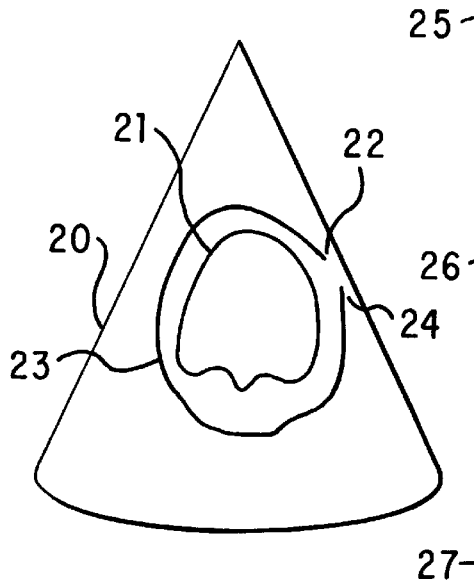
FIGS. 2(A) and 2(B) illustrate a curved anatomical M-Mode. The figure illustrates how the curved myocard in a short-axis view can be displayed versus time in a single M-Mode image.
Figure 2B:
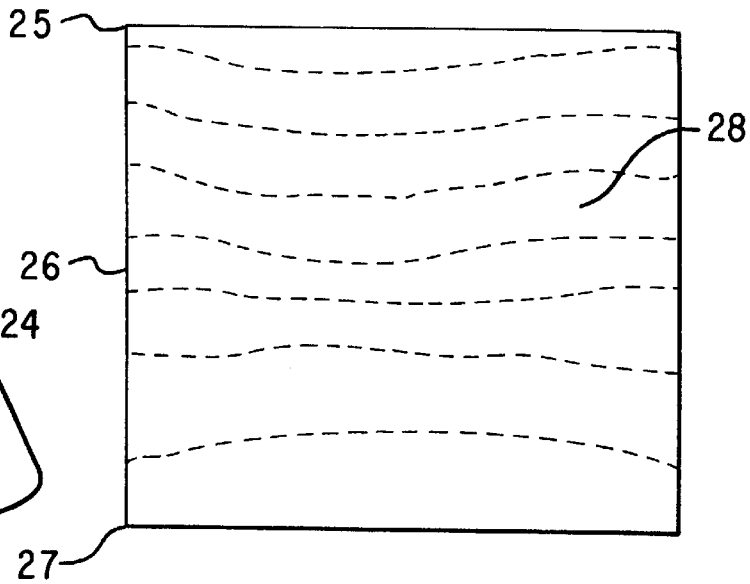

In the case of tissue velocity studies, it is interesting to analyze the velocity variations inside curved biological organs such as myocard. This invention teaches the construction of curved polygons that can be used to track curved organs and the extraction of temporal variations across these curved polygons. The polygons described and shown in the drawings can have arbitrary curved shapes being more or less irregular, but consisting in principle of a number of straight line edges, the number of which can be rather high—see, for example, polygon 22-23-24 in FIG. 2. In FIG. 2, an ultrasonic sector 20 is illustrated together with an example of a biological structure 21. The curved anatomical M-Mode polygon is illustrated extending from 22 through 23 and to 24. The associated curved anatomical M-Mode display is given by 28. The horizontal direction in 28 indicates the temporal variations in the same manner as 13. The vertical direction in 28 indicates the spatial position along the curved anatomical M-Mode polygon such that 25 corresponds with 22, 26 corresponds with 23 and 27 corresponds with 24. The computer processing techniques necessary for generating the curved anatomical M-Mode display are the same as the techniques taught in the U.S. Pat. No. 5,515,856. In this invention the spatial interpolation of tissue velocity information follows the curved polygon defining the curved anatomical M-Mode. If the curved anatomical M-Mode display 28 is sized such that it contains N different vertical positions, then the curved anatomical M-Mode polygon is sampled with N points distributed in an equidistant manner around the polygon.

Figure 3A:
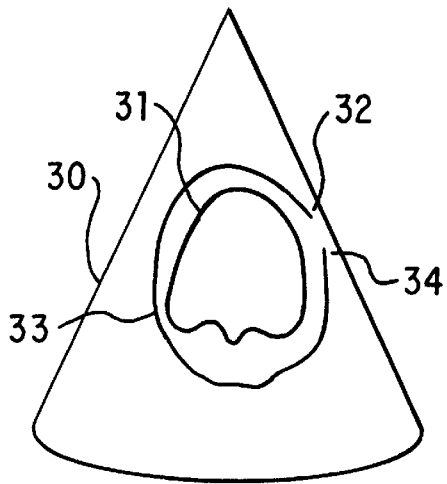
FIGS. 3(A) and 3(B) indicate how a curved anatomical M-Mode can be modified during a periodic motion such as the contraction of the heart such that extracted information belong to corresponding points in the moving organ.
Figure 3B:
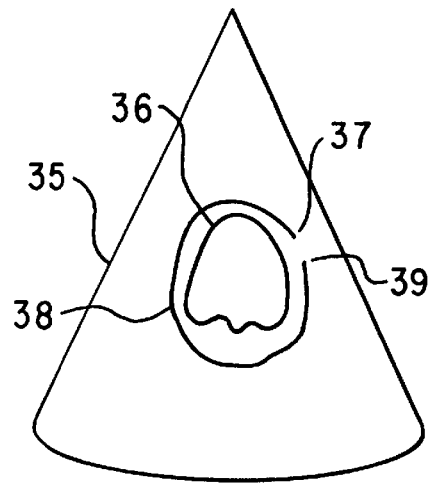

For moving organs such as the human heart or organs affected by other processes such as the blood pulse or respiration it can be useful to modify the position of the curved anatomical M-Mode polygon in order to let a given vertical coordinate in 28 track the same anatomical spatial position during the studied time interval. FIG. 3 illustrates an example of this technique where two frames from an image sequence of the heart 30 and 35 are shown. In this case the endocardial border contracts from 31 to 36 and the spatial position of the curved anatomical M-Mode polygon is adjusted accordingly. 32 has been moved to 37, 33 has been moved to 38 and 34 has been moved to 39. The positioning of the curved anatomical M-Mode polygon in the intermediate frames can be done either manually or through temporal interpolation of the spatial deformations provided by the user.

The spatial repositioning of the anatomical M-Mode or curved anatomical M-Mode can be automated by utilizing the tissue velocity information from at least one point. With 2-dimensional velocity estimates one or more fixation points in the tissue can be selected and the spatial positioning of the geometry repositioned in accordance with the movement of the fixation points.

Figure 4A:
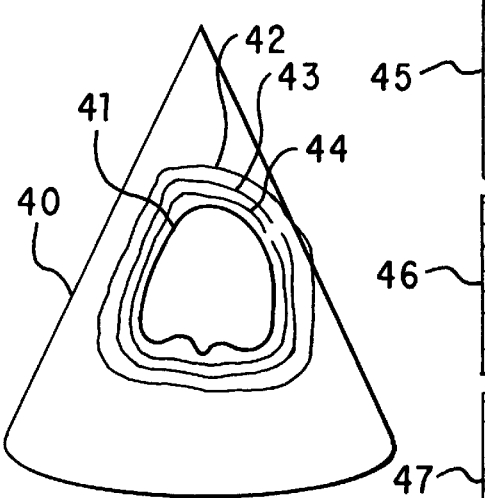
FIGS. 4(A) and 4(B) illustrate how a number of curved anatomical M-Modes can be positioned to extract the velocity variations perpendicular to the curved geometry. In this example the three curved anatomical M-Modes will display the velocity variations between endocard and epicard in myocard.
Figure 4B:
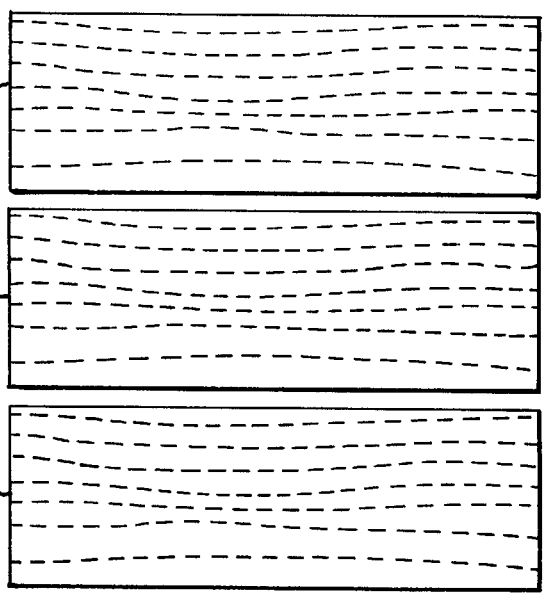

In FIG. 4 it is illustrated how multiple curved anatomical M-Modes can be utilized to also monitor the velocity variations in the direction perpendicular to the local geometry defined by the curved anatomical M-Mode polygon. The ultrasonic sector is given by 40 and an example of a biological structure is given by 41. Three curved anatomical M-Mode polygons are indicated by 42, 43 and 44. The associated curved anatomical M-Mode displays are given by 45, 46 and 47. The velocity variations between 45, 46 and 47 will show the velocity gradients between endocard and epicard in the example given in FIG. 4. These velocity gradients are important in for example diagnosis of rejection after heart transplantation.

In the case of 1-dimensional velocity estimates along the propagation direction of the ultrasonic beam the positioning of the curved anatomical M-Mode can also be utilized to estimate the true magnitude of the velocity field. In the case of myocardial contraction studies one can for example use the direction of the polygon and the assumption that the contraction is either perpendicular to the endocardial boundary or towards a fixed point in order to estimate a velocity with angular dependency compensation.

An application of this invention is to acquire data for several consecutive heart cycles during the injection of an ultrasonic contrast agent. This application will provide the clinician with a view of how the echogenicity properties of myocard are affected by the ultrasonic contrast agent and the timing information of these processes across the entire myocard in a single view.

In FIG. 5 it is illustrated how characteristic events in the tissue velocity evolutions can be identified in a curved anatomical M-Mode display. The imaged sector 50 contains an example of a biological structure 51 and a curved anatomical M-Mode polygon extending from 52 through 53 and to 54. The associated curved anatomical M-Mode display is shown in 58 with 55 corresponding to 52, 56 corresponding to 53 and 57 corresponding to 54. The solid line given by 510 indicates the localization of a characteristic event in the velocity evolutions along the horizontal lines in 58. The characteristic event could be a switch in the velocity direction, a peak in the velocity or a peak in the acceleration. In addition, the characteristic event can be identified in information derived from the primary velocity evolutions. One example of such a derived information is a tissue thickening estimator that can be obtained through spatial differences in the primary velocities. The characteristic events based on tissue thickening includes peak thickening, peak shortening and switch between thickening and shortening.

The characteristic event given by 510 can be localized in the velocity evolutions associated with all spatial coordinates within a region of interest. In FIG. 5 it is illustrated how a specific time interval between 59 and 511 is selected in the curved anatomical M-Mode display in order to study the characteristic event given by 510. FIG. 6 illustrates an ultrasonic sector 60 with an example of a biological structure 61 and an arbitrary spatial coordinate 62 within the spatial region of interest where tissue velocity estimates are performed. 68 illustrates the extracted velocity evolution for the point 62 during the selected time interval which can be identified by the technique illustrated in FIG. 5 or with a similar approach based on a straight line anatomical M-Mode as taught in U.S. Pat. No. 5,515,856. The time interval can also be a predetermined time span around the temporal location of the currently displayed ultrasonic image frame. Movies can hence be generated by repeating the computation for a number of frames in the acquisition sequence. By letting the selected time interval be the immediate past of the currently displayed ultrasonic image frame one can also make the computations based on the velocity evolutions in a real-time manner during acquisition of the ultrasonic image frames. For phenomena with long time delays across the spatial domain it can also be interesting to let the time interval be spatially dependent. 65 and 69 represent the start and end of the selected time interval. 64 and 63 is the range of velocities that are measured in the tissue. 66 and 67 are examples of possible characteristic events. 66 indicates a switch in the velocity direction and 67 indicates peak velocity. It should be noted that many characteristic events including shift in velocity direction, peak velocity and peak acceleration will for most spatial points be accurately temporally localized even if the velocity estimation is a 1-dimensional Doppler estimation along the propagation direction of the ultrasound beam. The velocity shift is for example only affected unless the real direction of the 3-dimensional velocity vector oscillates around a perpendicular orientation relative to the direction of the ultrasonic beam. The extracted timing information associated with characteristic events such as 66 and 67 can hence be made almost angle independent even for 1-dimensional Doppler estimates of tissue velocity.

Figure 7:
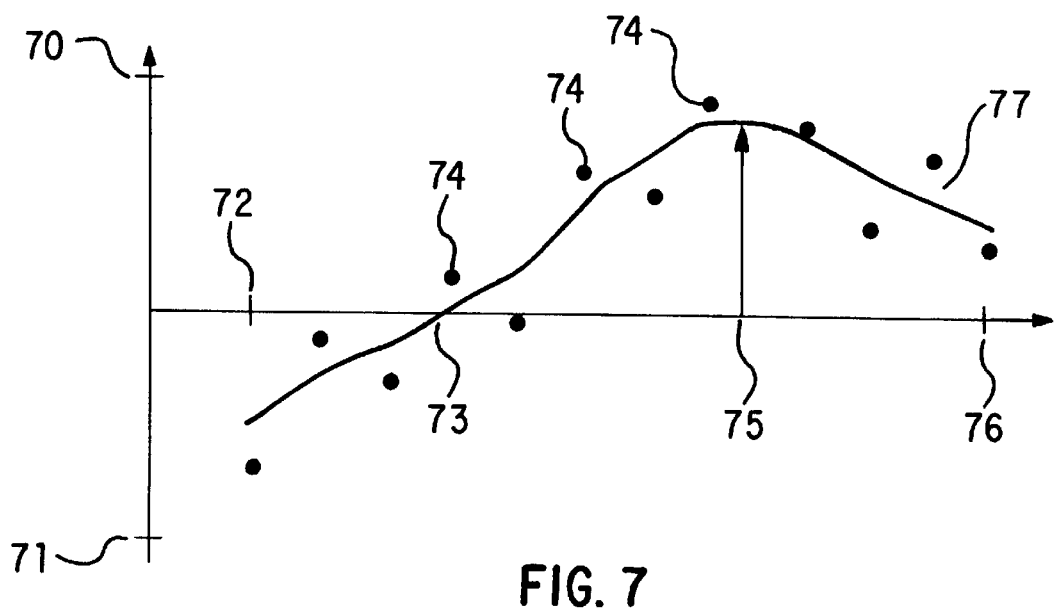
FIG. 7 illustrates how the original velocity measurements in the selected time interval for a given spatial coordinate is processed in order to remove artifacts and obtain reliable localization of characteristic points.

FIG. 7 illustrates how the numerical samples 74 extracted in the velocity evolution can be used to estimate a filtered and noise robust velocity evolution 77 in order to improve the reliability of identification of characteristic events. 72 and 76 represent the start and end of the selected time interval. 70 and 71 is the range of velocities that are measured in the tissue. In order to improve the robustness and precision of the identification of characteristic events, it is useful to filter the measured velocity evolutions as a function of space and/or time. The filters must suppress noise and cannot be biased in the temporal localization of events. A good candidate for such a filter is a temporal median filter that removes impulse noise and preserves edges and transitions in a good manner. A second candidate is to perform a regression of the measured velocities with a monotonically increasing or monotonically decreasing function in the selected time interval. Such a regression can be performed with only a constant number of operations per sample, gives strong noise suppression and is invariant for significant transitions.

Figure 8:
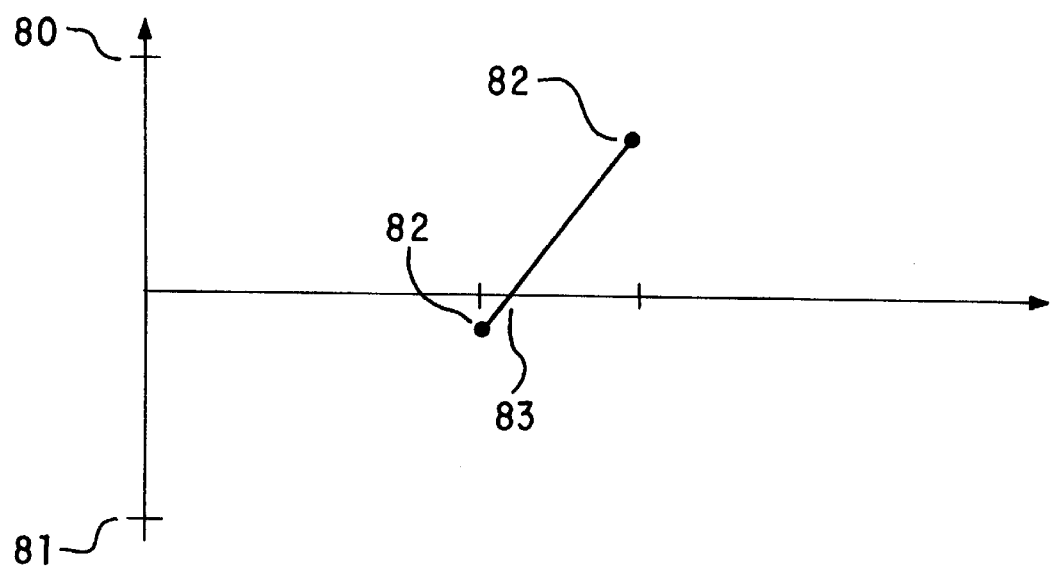
FIG. 8 illustrates how subpixel techniques can be applied to obtain improved accuracy in the temporal localization. In this case a zero-crossing is located as the interception of the x-axis with a linear approximation between the two adjacent measurements.

In the original velocity evolution 68 or the restored velocity evolution 77 the identification of characteristic events can be done with subpixel techniques in order to improve the accuracy of the temporal localization. FIG. 8 illustrates the subpixel technique in the case of a velocity shift detection. Two samples with opposite velocity direction are indicated by numeral 82. The real position of the velocity reversal can be estimated as the location of a linear approximation of the velocity evolution with the x-axis. Techniques for such subpixel localization are considered as background art and can be applied to all of the characteristic events taught in this invention. This subpixel technique improves the temporal localization compared to the framerate with typical factors between 3 and 10. As an example of such background art pertaining to subpixel localization, reference is made to the publication of Peter Seitz, "Optical Super resolution Using Solid State Cameras and Digital Signal Processings", *Optical Engineering*, 27(7), Jul. 1988.

There is a certain time delay in the acquisition of the data in a single ultrasonic frame. This time delay generates time delays between the various beams in the ultrasound image. If the scanning pattern of the ultrasound scanner is known, it is possible to compensate for this effect in the time localization of characteristic events by using the time corresponding to the ultrasonic beam covering the velocity evolution in stead of a common time for all beams in the ultrasonic image.

The resulting time delays as a function of space might contain individual erroneous detections. These errors can be removed or reduced by processing the time delays with a spatial filter. A median based filter is suitable because erroneous time localizations can be modeled as impulse noise in the time delay images.

Multiple time delay images as described in this invention can be combined to create images that quantify the time interval between two characteristic events. One example of this technique is to display the time difference between a velocity shift and the following peak velocity.

The display of the time delay images taught in this invention can be accomplished with many techniques in background art. The time delays can be converted to associated colors and displayed at the associated spatial position. The color assignment can be done such that multiple events can be separated. Examples of this approach include encoding of a switch from positive to negative velocity and a switch from negative to positive velocity in separate colors such that these two phenomena can be visually separated if both occur within the studied time interval. Furthermore, the time delay colors can be mixed transparently with the underlying ultrasonic image in order to allow the user to relate the time delays to the anatomical geometry.

The tissue velocity information extracted in an anatomical M-Mode or a curved anatomical M-Mode can be further processed to give a local estimate of the phase of the regional wall motion along the polygon or line associated with the anatomical M-Mode display. This technique is particularly useful in cardiac studies where a curved polygon can be positioned inside myocard and tissue velocity evolutions can be extracted for a number of points distributed across the polygon. For each point along the said polygon a complete velocity evolution is hence available and can be used to estimate the phase of the motion with background art for phase estimation. The said background art for phase estimation includes a Fourier analysis of the motion described by the temporal velocity variations. The said polygon can also be utilized to extract a curved anatomical M-Mode which in this case will show the basis for the phase estimation. Furthermore, the phase variations can be displayed together with the curved anatomical M-Mode display along the vertical axis in order to emphasize the relationship between the phase estimates and the curved anatomical M-Mode display. The techniques taught in this invention for repositioning of the polygon associated with a curved anatomical M-Mode display also applies to the polygon used for estimation of the phase of the regional wall motion. If a number of curved polygons are positioned between endocard and epicard or the polygon itself is drawn from endocard to epicard, it will be possible to study phase differences between endocard and epicard. The phase estimate is almost independent of the angle even if the tissue velocity is estimated with a 1-dimensional Doppler technique along the propagation direction of the ultrasound beam. Computing the dot product of the velocity with the direction of the ultrasound beam with a unit vector towards a center of gravity inside the cavity will remove the reflection in phase that otherwise can occur between upper and lower parts in the image. Artifacts can be expected if the true velocity vector is almost perpendicular to the direction of the ultrasound beam.

The phase estimate of the regional wall motion taught in this invention can be computed for every point in the imaged spatial scene. The resulting images give a spatial display of the phase of the regional wall motion that can be displayed with, for instance, the same techniques as those described for the spatial time delay images.

While the present invention has been shown and described with reference to the preferred embodiments presently contemplated as best modes for carrying out the invention, it is understood that various changes may be made in adapting the invention to different embodiments without departing from the broader inventive concepts disclosed herein and comprehended by the claims which follow.

What is claimed is:

1. A method for analysis and measurement of variations in tissue velocity, comprising the steps of:

acquiring a sequence of ultrasonic image frames covering a spatial region;

computing tissue thickening velocities for all points inside a spatial region of interest based on the information content in said ultrasonic frames;

generating thickening velocity evolutions based on the said computed velocities in a selected time interval associated with each point inside the said spatial region of interest;

extracting characteristic timing information from the said velocity evolutions; and displaying the said characteristic timing information at the associated spatial coordinates on a display unit.

2. The method according to claim 1, wherein the step of computing tissue velocities is based on a 1-dimensional velocity estimation with Doppler techniques along the propagation direction of the ultrasound beam.

3. The method according to claim 1, wherein the step of computing tissue velocities is based on a 2-dimensional velocity estimation with Doppler techniques along the propagation direction of two skewed ultrasound beams.

4. The method according to claim 1, wherein the step of computing tissue velocities is based on a spatial displacement correlation between subsequent ultrasonic image frames.

5. The method according to claim 1, further comprising the step of filtering the said velocity evolutions as a function of space and time in order to improve the robustness and precision of the velocity estimates.

6. The method according to claim 5, whereby said filtering includes a temporal median filter.

7. The method according to claim 5, whereby said filtering includes a temporal regression with monotonically increasing or monotonically decreasing functions.

8. The method according to claim 1, wherein the step of extracting characteristic timing information utilizes knowledge about the time associated with each of the individual beams in the ultrasonic image frames in order to avoid artifacts in the time localization due to the scanning delay across a single ultrasonic image frame.

9. The method according to claim 1, wherein the step of extracting characteristic timing information utilizes subpixel techniques in the temporal domain in order to improve the time resolution beyond the limitations given by the framerate.

10. The method according to claim 1, wherein the step of extracting characteristic timing information includes localization of the time associated with a switch in the velocity direction.

11. The method according to claim 1, wherein the step of extracting characteristic timing information includes localization of the time associated with peak velocity.

12. The method according to claim 1, wherein the step of extracting characteristic timing information includes localization of the time associated with peak acceleration.

13. The method according to claim 1, wherein the step of extracting characteristic timing information includes localization of the time associated with characteristic events in information that can be derived from the said velocity evolution.

14. The method according to claim 13, wherein the said information that can be derived from the said velocity evolution is a tissue thickening estimator.

15. The method according to claim 1, further comprising the step of filtering the extracted said characteristic timing information spatially in order to remove individual erroneous time localizations.

16. The method according to claim 1, wherein the step of extracting characteristic timing information includes computing time differences between two characteristic events in the velocity evolutions.

17. The method according to claim 1, wherein the said display of characteristic timing information includes a color range that encodes the various time delays in the extracted characteristic timing information.

18. The method according to claim 17, wherein the said color assignment is computed such that different characteristic events can be visually separated.

19. The method according to claim 18, wherein the said different characteristic events are switch from positive to negative velocity and switch from negative to positive velocity.

20. The method according to claim 17, wherein the said display is obtained by mixing the said time information colors transparently with the underlying ultrasonic image frame.

21. The method according to claim 1, further comprising the step of repeating the procedure for a number of temporally shifted time intervals and displaying the resulting images as an image sequence.

22. The method according to claim 21, wherein the process is done in real-time and the resulting images displayed during the acquisition of the ultrasonic image frames.

23. A method for generating curved anatomical M-Mode displays in ultrasonic investigations of living biological structures during movement employing an ultrasonic transducer, comprising the steps of:

acquiring a sequence of ultrasonic image frames covering a spatial region;

computing tissue velocities for all points inside a spatial region of interest based on the information content in said ultrasonic frames;

providing at least one curved anatomical M-Mode polygon positioned in relationship to said ultrasonic frames so as not to coincide with any straight line;

subjecting said ultrasonic image frames and said tissue velocities to computer processing on the basis of said at least one curved anatomical M-Mode polygon, whereby interpolation along said at least one curved anatomical M-Mode polygon is effected using values from said tissue velocities; and displaying the resulting computed curved anatomical M-Mode display on a display unit.

24. The method according to claim 23, further comprising the step of moving the position and orientation of said at least one curved anatomical M-Mode polygon in response to rhythmic movement of the biological structure.

25. The method according to claim 24, wherein the said rhythmic movement is computed automatically based on the tissue velocity estimates from at least one position in the said biological structure.

26. The method according to claim 23, wherein the local direction of the said curved anatomical M-Mode polygon is used to compensate for the angular dependency of velocity estimates based on Doppler techniques along the propagation direction of the ultrasound beam.

27. The method according to claim 23, further comprising the step of generating multiple curved anatomical M-Modes by offsetting the curved anatomical M-Mode polygon locally in a perpendicular direction relative to the polygon in order to image variations perpendicular to the local geometry of the curved anatomical M-Mode polygon.

28. The method according to claim 27, wherein the said biological structure is myocard and the said curved anatomical M-Mode polygons are positioned such that velocity variations between endocard and epicard can be monitored.

29. The method according to claim 23, wherein the said acquisition of ultrasonic image frames is performed in several consecutive heart cycles during the injection of an ultrasonic contrast agent.

30. The method according to claim 1 and 23, further comprising the step of providing means for selecting the said time interval based on the information content in the said curved anatomical M-Mode displays.

31. A method for computing regional phase information about the wall motion in ultrasonic investigations of the human heart employing an ultrasonic transducer, comprising the steps of:
- acquiring a sequence of ultrasonic image frames covering a spatial region;
- computing tissue velocities for all points inside a spatial region of interest based on the information content in said ultrasonic frames;
- providing at least one arbitrary polygon positioned in relationship to said ultrasonic frames;
- extracting the temporal evolution of the tissue velocities for a number of points distributed around the said polygon; and
- computing an estimate of the phase of the motion for said points based on said temporal evolutions of tissue velocities.

32. The method according to claim 31, wherein said polygon is also used to generate an anatomical M-Mode or a curved anatomical M-Mode.

33. The method according to claim 31, further comprising the step of moving the position and orientation of said polygon in response to the rhythmic movement of the heart.

34. The method according to claim 32, wherein the said rhythmic movement is computed automatically based on the tissue velocity estimates from at least one position in the heart.

35. The method according to claim 31, further comprising the step of computing the phase for a number of curved polygons positioned from endocard to epicard in order to calculate phase differences across myocard.

36. The method according to claim 32, wherein the said estimate of the phase of the motion is accomplished with a Fourier analysis of the said temporal tissue velocity evolutions.

37. A method for computing spatial regional phase images of the wall motion in ultrasonic investigations of the human heart employing an ultrasonic transducer, comprising the steps of:
- acquiring a sequence of ultrasonic image frames covering a spatial region;
- computing tissue thickening velocities for all points inside a spatial region of interest based on the information content in said ultrasonic frames;
- extracting the temporal evolution of the tissue thickening velocities for every point inside the said spatial region;
- computing an estimate of the phase of the motion for said points based on said temporal evolutions of tissue velocities; and
- displaying the resulting phase values as a spatial image.

38. The method according to claim 37, wherein the said estimate of the phase of the motion is accomplished with a Fourier analysis of the said temporal tissue velocity evolutions.

* * * * *